United States Patent [19]

Leary

[11] Patent Number: 4,545,390
[45] Date of Patent: Oct. 8, 1985

[54] STEERABLE GUIDE WIRE FOR BALLOON DILATATION PROCEDURE

[75] Inventor: James J. Leary, Woburn, Mass.

[73] Assignee: C. R. Bard, Inc., Murray Hill, N.J.

[21] Appl. No.: 421,315

[22] Filed: Sep. 22, 1982

[51] Int. Cl.⁴ .............................................. A61M 25/00
[52] U.S. Cl. .................... 128/772; 128/657; 128/344; 604/95; 604/96
[58] Field of Search ...................... 128/325, 344, 348.1, 128/656-658, 772; 604/95, 96, 170

[56] References Cited

U.S. PATENT DOCUMENTS

| | | | |
|---|---|---|---|
| 3,452,740 | 7/1969 | Muller | 128/772 |
| 3,467,101 | 9/1969 | Fogarty et al. | 128/348.1 |
| 3,547,103 | 12/1970 | Cook | 128/772 |
| 3,789,841 | 2/1974 | Antoshkiw | 128/772 |
| 4,033,331 | 7/1977 | Guss et al. | 128/657 |
| 4,195,637 | 4/1980 | Gruntzig et al. | 128/348.1 X |
| 4,215,703 | 8/1980 | Willson | 128/772 |
| 4,307,722 | 12/1981 | Evans | 128/344 |

Primary Examiner—Dalton L. Truluck
Attorney, Agent, or Firm—Wolf, Greenfield & Sacks

[57] ABSTRACT

A guide wire is provided to guide a very small diameter catheter, such as a coronary dilatation catheter used in coronary angioplasty techniques. The guide wire itself is of very small diameter, (under 0.020") yet is steerable and may be visualized fluoroscopically. The major portion of the guide wire is a small diameter flexible rod. The distal region of the rod is tapered. The tapered portion is surrounded by a helically wound spring which is brazed at its proximal and distal ends, to the base and tip, respectively, of the tapered region of the rod. A shorter segment of the spring extends beyond the distal end of the rod and serves as a highly flexible bumper to assure that the distal tip of the guide wire will not cause traumatic injury to the blood vessel. The distal region of the guide can be bent manually by the surgeon to a curved shape which it will tend to assume when relaxed. The distal region is flexible and can bend from the set curve to follow the contour of the blood vessel. The distal end of the wire can be steered by manipulation and rotation of the proximal end of the guide. At least the spring portion of the guide wire is formed from a material having a high degree of radiopacity to facilitate its fluoroscopic observation. Also disclosed is a combination of such a spring guide with a coronary dilatation catheter.

70 Claims, 5 Drawing Figures

STEERABLE GUIDE WIRE FOR BALLOON DILATATION PROCEDURE

BACKGROUND AND SUMMARY OF THE INVENTION

This invention relates to guide wires for use in small bore blood vessels such as those involved in cardiovascular surgical procedures. More particularly, the invention concerns a guide which can be steered into and along very narrow blood vessels (including naturally narrow vessels as well as stenosed vessels) to locate its distal end in a precise position. Once so placed, a catheter can be advanced over the guide wire directly to the particular site in the patient's cardiovascular system. The invention is of particular importance in coronary dilatation techniques where the catheter is itself very small in diameter and is difficult to advance and place deeply in the patient's cardiovascular system, as is the case when trying to reach a coronary artery.

Before the present invention there was no satisfactory guide wire for use with such small diameter catheters. Typically the procedure for advancing a dilatation catheter into the coronary artery has been to use a relatively stiff, large diameter, conventional coronary angiographic catheter as a guide through which the smaller diameter dilatation catheter is advanced. In that technique the relatively large diameter guide catheter is advanced and manipulated to locate its distal end at the entry to the coronary artery. The more slender, flexible dilatation catheter then is passed through the guide catheter so that the distal end of the dilatation catheter will exit from the guide catheter and, hopefully, will enter the entrance to the coronary artery. The technique, which is disclosed in U.S. Pat. No. 4,195,637 to Gruntzig, requires that the dilatation catheter be pushed through the guide catheter and then into and through the coronary artery. Typically it is required to push the dilatation catheter so that its balloon passes through or into the mass of stenotic material which obstructs the coronary artery. Because of the slender, flexible and delicate nature of the coronary dilatation catheter such advancement and placement of the dilatation catheter is a delicate, difficult procedure calling for a great deal of skill, care and patience.

While suggestions have been made to use a guide wire to advance such a slender catheter as a coronary dilatation catheter, no suitable device was known which could serve properly as a guide wire while being small enough to permit the relatively small diameter dilatation catheter to be slipped over and advanced along the guide wire. Because the guide wire of the type of which the present invention is concerned is much smaller than a conventional guide wire (of the order of 0.018" diameter as compared to a conventional guide wire approximately 0.038" diameter), numerous additional difficulties in the construction and use of such a guide wire are presented. For example, using a smaller guide wire typically tends to result in reduced stiffness and, therefore, is more difficult to control and manipulate. A smaller diameter guide wire typically may be expected to be more fragile and more susceptible to breakage. Less torque can be transmitted along a smaller diameter, more delicate guide wire, particularly a guide wire which utilizes conventional construction in which substantially the full length of the guide wire is in the form of a helically wound spring wire. Additionally, a smaller guide wire is more difficult to observe fluoroscopically. That problem is pronounced particularly with heavier patients whose additional tissue makes it more difficult to observe fluoroscopically the position of the guide wire. It may be possible to observe fluoroscopically the position of a smaller guide wire in such a patient.

It is among the general objects of the invention to provide a guide wire construction which is of very small diameter, suitable for use with catheters intended to be advanced into small bore arteries such as, for example, a coronary dilatation balloon catheter, which avoids the foregoing, and other difficulties.

In accordance with the present invention the guide wire includes a main rod or wire of a small diameter which extends substantially the full length of the guide wire. The main wire is of uniform diameter except for the distal portion which is provided with a progressively narrowing taper. The tapered distal portion of the main wire is surrounded by a helically coiled spring. In the preferred embodiment the proximal end of the spring is secured to the main wire where the wire begins to taper and the distal end of the spring is secured to the distal end of the main wire, where the taper is most narrow. The distal end of the helical spring extends slightly beyond the distal tip of the main wire, for approximately one centimeter to define a spring extension. The spring extension tip is highly flexible and delicate and may bend and flex easily. It serves as a soft, flexible, resilient bumper for the distal tip of the guide wire, thereby minimizing the chance of trauma or injury to the blood vessel. The main spring and the distal bumper spring are formed from a material having a high radiopacity. Although not essential, the main wire also may be formed from a material having a high degree of radiopacity.

A high degree of torque control is provided by the rotationally rigid wire which makes up the major portion of the length of the guide wire. The use of a rotationally rigid wire over the major length of the guide wire assures that most of the torque applied at the proximal end will be transmitted fully to the distal region, unlike more conventional guide wires in which the torque tends to twist and distort the guide wire.

The distal region of the guide wire which includes the tapered safety wire and surrounding spring may be bent manually by the surgeon to a predetermined curve so that the distal portion of the guide will be biased toward that curved shape. The curve enables the guide to be advanced selectively into various branches at blood vessel bifurcates by controlling the rotation of the wire from its proximal end. The progressive taper at the distal region of the wire provides for a distal region with a main spring which increases in flexibility as it approaches the distal tip. Risk of trauma to the blood vessel is minimized by the highly flexible short bumper spring extension at the distal tip of the device.

Another aspect of the invention relates to the configuration of the dilatation catheter in combination with the small diameter guide wire. The catheter is constructed so as to have a main lumen which is dimensioned and shaped with respect to the guide wire so that even when the guide wire is in place within the main lumen there still is adequate cross-sectional flow area in the lumen. Thus the guide wire need not be removed in order to administer fluids to the patient or to take pressure measurements or the like.

It is among the objects of the invention to provide a small diameter guide wire which provides a high degree of steerable control and which may be placed with precision so as to serve as a guide for a catheter.

Another object of the invention is to provide a small diameter guide wire of the type described in which the distal portion may be pre-bent into a predetermined curve to facilitate steering of the wire by rotational control from the proximal end of the guide wire.

A further object of the invention is to provide a small diameter guide wire in which the distal portion is of increasing flexibility.

Another object of the invention is to provide a small diameter guide wire which has reduced risk of trauma to the inner surface of small bore blood vessels.

A further object of the invention is to provide small diameter guide wire having increased fluoroscopic visibility.

Another object of the invention is to provide a small diameter guide wire suitable particularly for use with balloon dilatation coronary catheters.

Still another object of the invention is to provide an improved combination of balloon dilatation catheter and guiding means therefor to advance the balloon dilatation catheter.

A further object of the invention is to provide a guide wire for use with a balloon dilatation catheter which facilitates the speed with which a vascular or coronary dilatation procedure can be performed.

Still another object of the invention is to provide a combination dilatation catheter and guide wire therefor in which the guide wire need not be removed in order to deliver fluids through the catheter or to make pressure measurements.

DESCRIPTION OF THE DRAWINGS

The foregoing and other objects and advantages of the invention will be appreciated more fully from the following further description thereof, with reference to the accompanying drawings wherein.

DESCRIPTION OF THE PREFERRED EMBODIMENT

Figure 1:
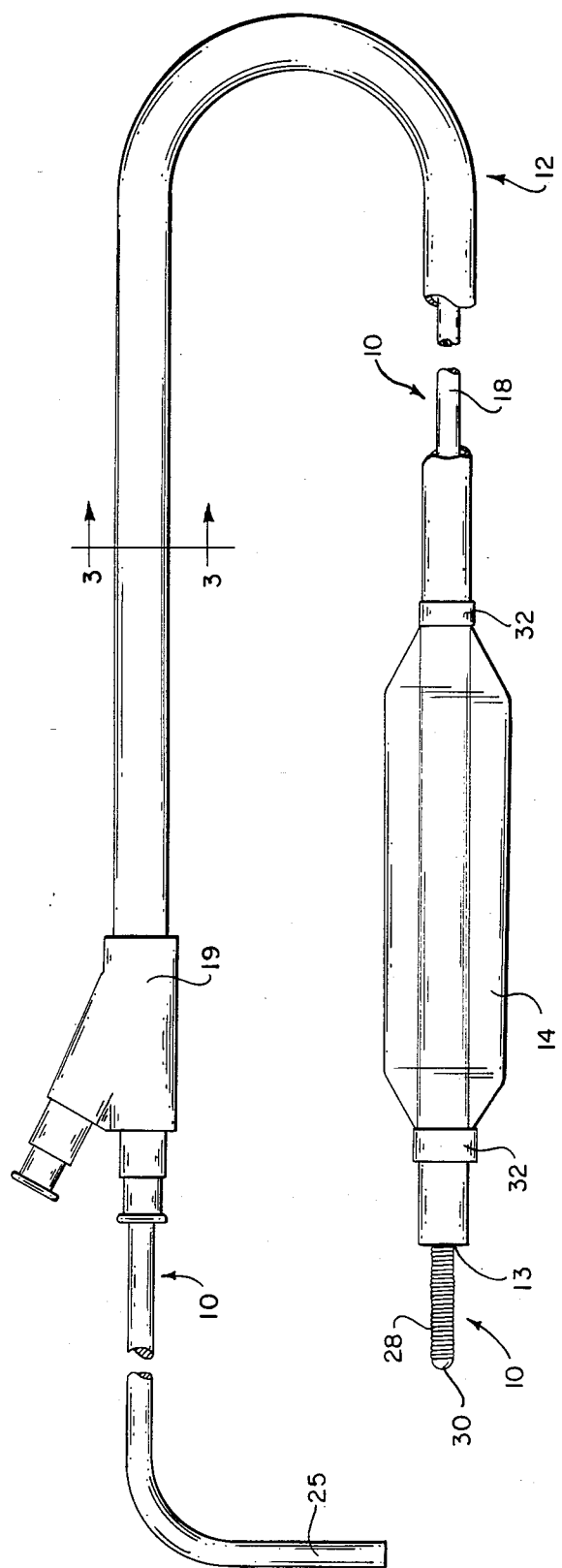
FIG. 1 is an illustration of a guide wire of the present invention in combination with a balloon dilatation catheter.

FIG. 1 shows the guide wire 10 of the present invention in combination with a balloon dilatation catheter 12 of the general type described in the aforementioned Gruntzig patent. The dilatation catheter 12, particularly when it is intended for use in a coronary artery, is relatively slender and, for example, may have an outer diameter of the order of 0.050". The inner diameters of its lumens, of course, are even smaller and its main lumen may be the order of 0.022" diameter at its smallest cross-sectional dimension. The dilatation catheter has a dilatation balloon 14 at its distal end and a central lumen 16 (See FIG. 3) which is used typically to deliver liquids such as radiopaque dyes or anticoagulants and also may be used to make pressure measurements. The central lumen 16 opens at an outlet 13 at the distal tip. As shown in further detail in FIG. 3 the dilatation catheter also is provided with an inflation lumen 17 which is smaller and communicates with the interior of the balloon 14 to inflate and deflate the balloon. The proximal end of the catheter may be provided with a Y-fitting 19 to provide communication at the proximal end of the catheter to each of the central lumen 16 and inflation lumen 17.

As described in the aforementioned Gruntzig patent, such a catheter typically has been guided to the entrance of the coronary artery by a relatively large diameter guide catheter having an internal lumen large enough to accommodate the outer diameter of the dilatation catheter. Such a guide catheter can, at best, only lead the dilatation catheter to the entry to a coronary artery because the guide catheter typically is too large to make any significant entry into the coronary artery. Because the relatively large guide catheter cannot be advanced into and controllably manipulated through the coronary arteries, the prior practice has required that the dilatation catheter be pushed into and through the coronary artery to reach the area to be treated. Because of the relatively small diameter and delicate, flexible construction of the dilatation catheter, advancement of the catheter into a narrow coronary artery, and particularly one which is obstructed, often is quite difficult and takes a considerable amount of skill. Sometimes it simply is not possible to reach as deeply into the coronary artery as might be desired.

Also among the difficulties which may be presented with the prior technique of using a guide catheter is that because of the difficulty which may be encountered by trying to push and advance the balloon dilatation catheter through the coronary artery, more surgical time may be used than would be desirable. In this regard it is desirable that such dilatation procedures be performed as quickly as possible so that the artery is obstructed as briefly as possible.

In accordance with the present invention, a guide wire 10 is advanced through the patient's vascular system, its direction being controlled and fluoroscopically monitored by the surgeon, until its distal end is at the desired location. Because the wire is very small in diameter it does not present any substantial obstruction to blood flow in the blood vessel. Then, the dilatation catheter 12 is advanced over the guide wire with the wire being received in the main lumen 16 of the catheter 12. The guide wire thus simply and automatically guides the catheter directly to the intended region, without requiring difficult, time consuming manipulations.

Figure 3:
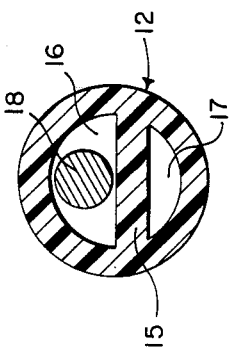
FIG. 3 is a sectional illustration of a balloon dilatation catheter and guide wire in accordance with the invention as seen in section along the line 3—3 of FIG. 1.

As shown in further detail in FIG. 3 the dilatation catheter is formed from extruded plastic and has an internal web 15 which separates and defines the main and inflation lumens 16, 17. As shown, the inflation lumen 17 is smaller than the main lumen 16. Both of the lumens 16, 17 are generally D-shaped cross-section. The main lumen 16 extends to the distal tip and terminates in opening 13. The inflation lumen 17 leads to the balloon. In the illustrative embodiment of the invention, the main lumen has a minimum dimension which is just slightly greater than the diameter of the guide wire 10. The maximum cross-sectional dimension which, in the illustrative embodiment consists of the straight wall portion of the D-shaped lumen 16 is substantially larger than the cross-section of the guide wire 10. Thus, when the guide wire 10 is disposed within the main lumen 16 there will be substantial voids through the central lumen 16, on opposite sides of the guide wire 10 through which fluids may be administered to the patient and through which blood pressure measurements may be taken. Such fluids may be administered and pressure measurements may be taken without removing the guide wire at all thereby contributing to the reduced time required for for procedures in accordance with the invention. By way of example, the cross-section of the guide wire 10 preferably is of the order of no more than about fifty percent of the cross-sectional area of the main lumen 16.

Figure 2:
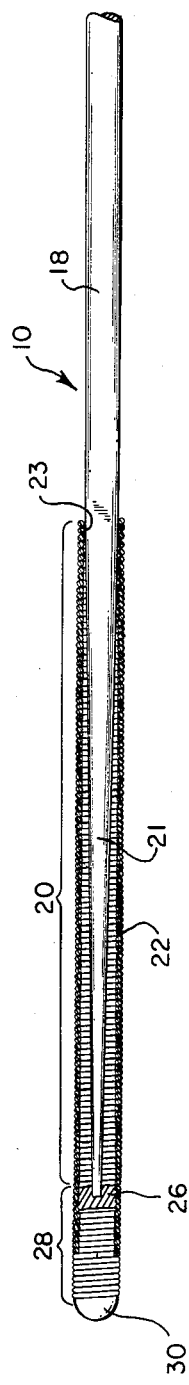
FIG. 2 is a fragmented and sectional illustration of a guide wire in accordance with the invention, out of scale for purposes of ease of explanation.
Figure 2A:
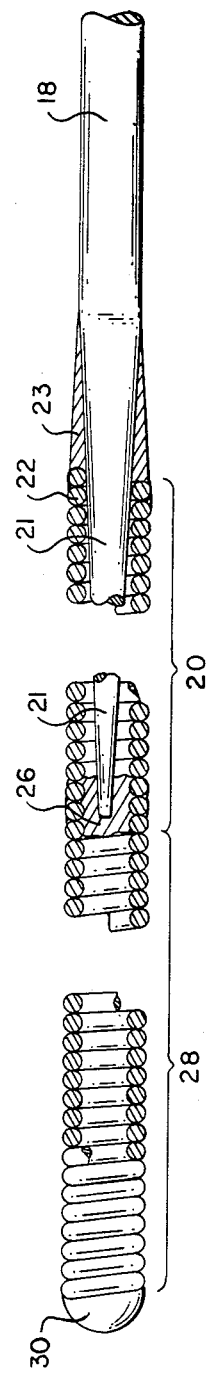
FIG. 2A is a sectional, fragmented, englarged illustration of the guide wire of FIG. 2 but shown more nearly to scale.

FIG. 2 shows the construction of the guide wire in further detail although portions are not to scale for ease of explanation and illustration. FIG. 2A illustrates portions of the guide wire in enlarged, more scaled detail. The guide wire 10 typically will be approximately 175 centimeters long so that it may be introduced either through the femoral or brachial arteries and have ample length to reach the patient's coronary region. The guide wire 10 includes a small diameter main wire 18. Main wire 18 can be solid or tubular, as long as it is rigid torsionally so that it may transmit fully to the distal end a rotational motion imparted to the proximal end. Unlike conventional guide wires which are formed substantially from elongate helical springs and which do not provide good torque transmission from the proximal to distal end, the present invention provides a very high degree of torque transmission from the proximal to its distal end because the rotationally rigid main wire 18 will have relatively little twist as its proximal end is rotated. Practically all rotation applied to the proximal end will be transmitted quickly to the very distal tip of the guide wire. The main wire 18 may be solid, as shown in the drawings, or may be in the form of a hollow tube. In either case it is rotationally rigid so that the maximum amount of torque applied at the proximal end can be transmitted to the distal end.

The main wire 18 is of uniform diameter except the distal region 20 of the main wire is provided with a taper. The distal tapered portion 21 may be approximately twenty centimeters long and may be formed by grinding. It is important that the taper be regular and uniform without any sharp transitions which might form stress concentrations or tendencies to kink when the wire is bent in use, as will be described.

The distal tapered portion 20 of the main wire 18 is surrounded by a helically wound spring 22 which is slightly more than twenty centimeters long. The proximal end of the spring 22 is secured to the main wire, as by brazing at a proximal connection (indicated at 23). The distal end of the main spring 22 is secured to the distal end of the tapered portion 20, also by a brazed distal connection connection such as suggested at 26. The distal tapered portion 21 thus acts as a safety wire for the spring 22. Additionally, the uniform tapering configuration of the distal tapered portion 20 results in an arrangement by which the distal region has an increasing uniform flexibility along the length of the spring.

The distal tip of the guide wire 10 is formed by an extension 28 of the spring 22 which is relatively short and extends approximately one centimeter beyond the distal end of the wire 18. The spring extension 28 is very flexible and has, at its most distal tip, a weld 30 which is smoothly rounded off. The spring extension 28 serves as a flexible bumper at the leading end of the advancing guide wire, and minimizes the risk of trauma or injury to the delicate internal surfaces of the artery. Should the distal end of the guide wire 10 be advanced toward a blood vessel surface at too sharp an angle or otherwise in a manner which otherwise might present some risk of trauma, the bumper spring 28, being highly flexible and with a very smooth leading end, tends to soften the contact and also tends to guide the spring 22 in a direction which will avoid trauma to the blood vessel.

At least the main spring 22 and bumper spring 28 are formed from a material having a high degree of radiopacity. For example, spring material of an alloy consisting of approximately 92 percent platinum and 8 percent tungsten has been found to provide satisfactory radiopacity while providing ductility and good spring flexibility. The spring wire may be wound from wire 0.004" diameter. The outer diameter of the main spring portion 22 may be of the order of 0.018" diameter. The main wire 18 may be of the order of 0.016" diameter. It is desirable to maintain the outer diameter of the spring 22 as close to the outer diameter of main wire 18 as is practically possible and to provide as smooth a transition as is practical. Thus, the outer diameter of the spring should not be substantially greater, if at all, than the outer diameter of the main wire 18. Additionally, having the main wire 18 with an outer diameter as close to the outer diameter of the main spring is desirable so that the main wire 18 may have the maximum torsional rigidity.

The platinum-tungsten alloy also is quite satisfactory in that the tapered distal region can be bent manually by the surgeon and will retain its bent configuration when relaxed. This enables the guide wire to be controllably steered by rotation of the guide wire to direct the curved distal end selectively into various arterial branches. Rotational control of the guide wire may be enhanced by bending the proximal end of the wire 18 to form somewhat of a handle, as suggested at 25 in FIG. 1.

Figure 4:
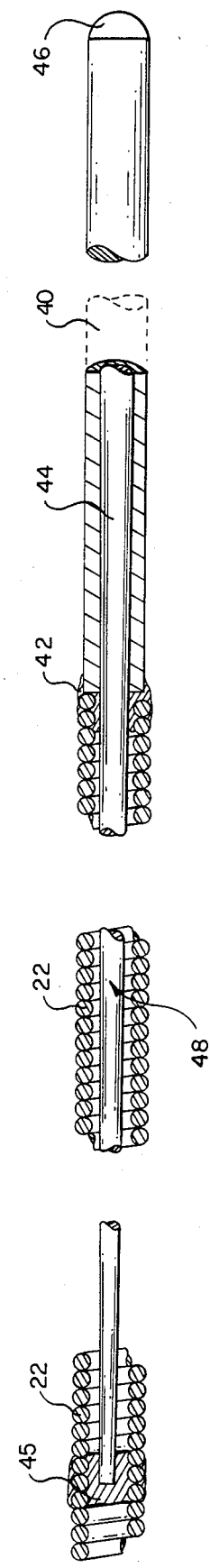
FIG. 4 is an illustration similar to FIG. 2A of a modified embodiment of the guide wire.

FIG. 4 is an illustration of a modified embodiment of the guide wire. In this embodiment the proximal portion of the wire is formed from a composite including a length of hollow outer hypodermic tubing 40 to which the proximal end of the spring 22 is brazed, as at 42. A safety wire 44 extends through both the hypodermic tubing 40 and into the interior of the spring 22 where it is attached to a more distal region of the spring 22, at 45. Safety wire 44 is secured at its proximal end by a weld 46 to the hypodermic tube.

In this embodiment the taper of the wire 44 within the spring 22 begins at a location, indicated at 48, between the ends of the spring 22. Thus, in contrast with the previously described embodiment, this embodiment utilizes an arrangement in which that portion of the wire 44 which extends from the junction 42 to the region 48 will display a substantially uniform degree of flexibility whereas the remaining more distal portion of the wire 44, extending from region 48 to connection 45 will display progressively increasing flexibility. This alternate configuration is in all other respects the same as the previously described embodiment.

In use, the surgeon may bend the distal region of the guide wire so that it will be biased toward and will assume somewhat of a curve when relaxed. When advanced through the patient's artery the degree of resilience at the distal region of the wire is such that the wire will straighten and follow the path of the artery quite easily. The progressively increased flexibility resulting from the continuous taper at the distal region of the device enhances the ability of the guide wire to flex from the pre-bent biased curve and follow the path of the blood vessel.

The relatively high degree of radiopacity of the distal region of the wire enhances the fluoroscopic imaging of the wire as it is advanced through the patient's artery. As indicated above, this is particularly important when the patient is somewhat obese which tends to make fluoroscopic observation of a slender guide wire quite difficult, and sometimes impossible with conventional guide wires.

When the distal end of the pre-bent, biased guide is at an arterial fork, the surgeon can steer it into one branch or the other selectively by rotation of the guide wire by manipulating it from the proximal end. As described, the solid wire configuration which extends over the major proportion of the guide provides for a high degree of torque transmission and rapid response at the distal end. As a result, the advancement of the guide wire can be observed with clarity and its direction steered quickly and responsively, all of which tends to reduce the amount of time that the operation takes.

The procedure for using the guide wire and dilatation catheter in accordance with the present invention involves initial placement and location of a conventional guide catheter so that its distal end is adjacent to the coronary ostium, the entry to the coronary artery. The dilatation catheter is prepared with the guide wire in place, extending through the main lumen 16 so that about two centimeters of the distal tip of the guide wire project distally beyond the outlet 13 of the dilatation catheter. This assembly of dilatation catheter and guide wire then is pushed through the guide catheter into the coronary artery, with the guide wire being used to manipulate the dilatation catheter selectively into deeper and smaller coronary arteries. In this regard it should be noted that the simultaneous advancement of the dilatation catheter and guide wire is performed with the distal portion of the guide wire projecting distally beyond the outlet 13 of the dilatation catheter. The projecting end of the guide wire tends to bias toward the curved configuration which the surgeon will have preset as he desires. As the stenosis is approached it may be desirable to advance the guide wire independently of the dilatation catheter to locate the guide wire with a high degree of precision with respect to the stenosis. The guide wire is advanced to that site by a combination of pushing and rotation or steering of its proximal end. Once the guide wire is in place across the stenosis the dilatation catheter then may be advanced over the guide wire to a point where the balloon is positioned within the obstruction. This can be verified fluoroscopically because of the highly radiopaque characteristic of the spring and also by injecting radiopaque dye through the main lumen 16. Additionally, verification may be determined by monitoring the drop in arterial pressure through the lumen 16 as the balloon is advanced across the stenosis.

The dilatation catheter typically is provided with radiopaque rings 32 which also facilitate fluoroscopic monitoring of its progress and position. When the balloon dilatation catheter has been advanced so that the balloon is located as desired, the balloon then may be inflated as described in the Gruntzig patent to dilate the stenosis and expand the vascular lumen. During the procedure liquids such as radiopaque dyes, heparin may be administered to the patient or pressure monitoring readings can be taken without removing the guide wire.

Thus, I have described an improved system for guiding vascular catheters (and particularly dilatation catheters) to a predetermined site in the patient's vascular system. The invention results in a highly controllable and steerable guide having a high degree of radiopacity to facilitate fluoroscopic observation even with obese patients. Moreover, these advantages have been achieved in a guide wire which reduces the chance of traumatic injury to the delicate interior of the arteries. Notwithstanding its small diameter and delicate nature the distal end can be pre-formed to a predetermined biased curve yet it will not develope stress points or tend to kink. The invention enables dilatation procedures to be performed more radidly with reduced time during which the dilatation catheter resides in the blood vessel.

It should be understood, however, that the foregoing description of the invention is intended merely to be illustrative thereof and that other embodiments and modifications of the invention may be apparent to those skilled in the art without departing from its spirit.

Having thus described the invention what I desire to claim and secure by Letters Patent is:

1. A steerable small diameter guide wire comprising:
   a main wire having a tapered distal region;
   a helically wound spring at the distal region of the main wire, the tapered region of the main wire being received within the spring, the proximal end of the spring being secured to the main wire at a proximal connection adjacent to the region where the main wire begins to taper;
   the distal end of the main wire terminating short of the distal end of the spring and being secured to the spring at a distal connection;
   the spring having a relatively short portion which extends distally beyond the distal end of the main wire, the distally extending short portion being highly flexible and terminating in a smoothly surfaced rounded tip;
   each of the main wire and the spring having an outer diameter which is no greater than about 0.020 inches, the diameter of the spring being not substantially greater than the diameter of the main wire;
   the guide wire having a distal region which is adapted to be bent to a set curved configuration and to retain that set curve when the distal region of the guide wire is relaxed, said distal region of the guide wire being sufficiently flexible so as to adapt to and follow the contours of a patient's blood vessel;
   said guide wire having means sufficiently torsionally rigid along its length for transmitting to the distal end of the guide wire substantially all of the angular rotation applied to the proximal end of the guide wire thereby enabling the curved distal end of the guide wire to be controllably directed to selected branches of a patient's vascular system.

2. A guide wire as defined in claim 1 wherein at least the spring is formed from a material having a high radiopacity.

3. A guide wire as defined in claim 2 wherein the spring is formed from an alloy which includes approximately 92% platinum and 8% tungsten.

4. A steerable small diameter guide wire as defined in claim 1 wherein the distal region of the main wire is tapered progressively toward the distal end of the wire and wherein said tapered region of the main wire extends smoothly and uniformly from the more proximal portions of the main wire and defining a smooth transition from the untapered to the tapered portion.

5. A steerable small diameter guide wire as defined in claim 1 wherein the outer diameter of each of the spring and the main wire are substantially the same.

6. A guide wire as defined in claim 1 in which only a minor portion of the overall length of the guide wire comprises the spring.

7. A guide wire as defined in claim 1 further comprising:
said guide wire being of a length of the order of 175 centimeters;
the spring and tapered region of the main wire extending over the most distal approximately 20 centimeters of the guide wire;
the distal extension of the spring being approximately one centimeter long.

8. A small diameter guide wire as defined in claim 1 further comprising:
said tapered region of the main wire beginning its taper at a location which is intermediate the proximal and distal ends of the spring.

9. A set for introducing a balloon dilatation catheter and for performing a balloon dilatation in a blood vessel comprising:
a guide wire as defined in claim 1;
a balloon dilatation catheter having a main lumen which is receptive to the guide wire, said main lumen being open at the distal end of the catheter.

10. A set as defined in claim 9 wherein the main lumen in the balloon dilatation catheter is larger in cross-section than the guide wire whereby a flow passage may be maintained within the balloon catheter for infusion of liquids and pressure measurements without requiring removal of the guide wire.

11. A set as defined in claim 10 wherein the main lumen has a different cross-sectional shape than that of the guide wire.

12. A set as defined in claim 11 wherein the guide wire is circular in cross-section and the main lumen of the catheter is D-shaped in cross-section.

13. A set as defined in claim 9 wherein the outer diameter of the dilatation catheter is not greater than of the order of 0.050 inches.

14. A set as defined in claim 10 wherein said guide wire is circular in cross-section and wherein said main lumen is non-circular in cross-section.

15. A set as defined in claim 10 wherein the cross-section defined by the guide wire is not greater than about 50% of the cross-sectional area of the main lumen in the catheter.

16. A set of a small diameter catheter and steerable guide wire for use therewith comprising:
a guide wire as defined in claim 1, and
a catheter having a lumen receptive to the guide wire, the lumen being open at the distal end of the catheter, said catheter having an outer diameter not greater than of the order of 0.050 inches.

17. A guide wire as defined in claim 1 further comprising: the taper at the distal region of the main wire being continuous.

18. A guide wire as defined in claim 1 wherein said torsionally rigid means comprises said main wire being formed from a solid rod.

19. A guide wire as defined in claim 1 wherein said torsionally rigid means comprises said main wire being formed from a solid walled tube.

20. A guide wire as defined in claim 1 wherein the spring is formed from an alloy which includes approximately 92 percent platinum and 8 percent tungsten.

21. A small diameter steerable guide wire comprising:
a main wire having a distal region;
a helically wound spring connected to the main wire at the distal region and receiving the distal region therein;
said guide wire being constructed and arranged so that the portion thereof located proximally of the distal region of the main wire is of substantially uniform flexibility along its length;
that portion of the guide wire which includes the distal region of the main wire and that portion of the helically wound spring which surrounds the distal region being of increasing flexibility in a distal direction
the spring having a distal extension which extends beyond the distal end of the main wire, the distal extension being of substantially uniform flexibility along its length, said distal extension being the most flexible of all of said portions of the guide wire;
the main wire and spring having substantially the same outer diameter, said diameter being no greater than about 0.020 inches;
that portion of the guide wire which includes the distal region of the main wire being adapted to be bent to a set curved configuration but being sufficiently flexible from said set curved configuration so as to adapt to and follow the contours of a patient's blood vessel;
the guide wire having means sufficiently torsionally rigid along its length for transmitting to the distal end of the guide wire substantially all of the angular rotation applied to the proximal end of the guide wire thereby enabling said guide wire with a set curved configuration at its distal region to be controllably directed to selected branches of a patient's vascular system.

22. A guide wire as defined in claim 21 further comprising: the distal region of the main wire being constructed so that it is more flexible at its distal end than at its proximal end.

23. A guide wire as defined in claim 22 wherein the distal region of the main wire is tapered in the distal direction.

24. A guide wire as defined in claim 23 wherein the taper is substantially continuous.

25. A set for introducing a balloon dilatation catheter and for performing a balloon dilatation in a blood vessel comprising:
a guide wire as defined in claim 21; and
a balloon dilatation catheter having a main lumen which is receptive to the guide wire, said main lumen being open at the distal end of the catheter.

26. A set as defined in claim 25 wherein the main lumen in the balloon dilatation catheter is larger in cross-section than the guide wire whereby a flow passage may be maintained within the balloon catheter for infusion of liquids and pressure measurements without requiring removal of the guide wire.

27. A set as defined in claim 26 wherein the main lumen has a different cross-sectional shape than that of the guide wire.

28. A set as defined in claim 27 wherein the guide wire is circular is cross-section and the main lumen of the catheter is D-shaped in cross-section.

29. A set as defined in claim 25 wherein the outer diameter of the dilatation catheter is not greater than of the order 0.050 inches.

30. A set as defined in claim 26 wherein said guide wire is circular in cross-section and wherein said main lumen is non circular in cross-section.

31. A set as defined in claim 26 wherein the cross-section defined by the guide wire is not greater than about 50 percent of the cross-sectional area of the main lumen in the catheter.

32. A small diameter steerable guide wire having a proximal end and a distal end comprising:
   a main wire having a distal region which is tapered toward the distal end of the wire;
   a helically wound spring at the distal region of the main wire, the tapered portion of the main wire being received within the spring, the spring having a proximal end secured to the main wire at a proximal connection adjacent to the region where the main wire begins to taper;
   the distal end of the main wire being secured to the spring at a location distal of said proximal connection;
   each of said main wire and spring having an outer diameter which is no greater than about 0.020 inches, the diameter of the spring being not substantially greater than the diameter of the main wire;
   the distal end of the guide wire being adapted to be bent to a set curved configuration and to retain that set curved configuration when relaxed, said distal end being sufficiently flexible so as to adapt to and follow the contours of a patient's blood vessel;
   the guide wire having means sufficiently torsionally rigid along its length for transmitting to the distal end of the guide wire substantially all of the angular rotation applied to the proximal end of the guide wire thereby enabling said guide wire with prebent distal end to be controllably directed to selected branches of a patient's vascular system.

33. A small diameter steerable guide wire as defined in claim 32 wherein the outer diameter of each of the main wire and spring are substantially the same.

34. A small diameter steerable guide wire as defined in claim 32 wherein at least the spring is formed from a material having a high radiopacity.

35. A steerable small diameter guide wire as defined in claim 32 further comprising:
   said guide wire being of a length of the order of 175 centimeters;
   the spring and tapered portion extending over the most distal approximately 20 centimeters of the guide wire.

36. A set of a small diameter catheter and steerable guide wire for use therewith comprising:
   a guide wire as defined in claim 32; and
   a catheter having a lumen receptive to the guide wire, said catheter having an outer diameter not greater than of the order of 0.050 inches.

37. A set as defined in claim 36 wherein said catheter comprises a balloon dilatation catheter.

38. A set as defined in claim 37 wherein the catheter has a main lumen which is open at the distal end of the catheter, the main lumen being larger in cross-section than the guide wire whereby a flow passage may be maintained within the balloon catheter for infusion of liquids and pressure measurement without requiring removal of the guide wire.

39. A set as defined in claim 38 wherein the main lumen has a different cross-sectional shape than that of the guide wire.

40. A set as defined in claim 39 wherein the guide wire is circular in cross-section and the main lumen of the catheter is D-shaped in cross-section.

41. A set as defined in claim 39 wherein the guide wire is circular and the lumen is non-circular.

42. A set as defined in claim 38 wherein the cross-sectional area of the guide wire is not greater than 50% of the cross-sectional area of the lumen.

43. A guide wire as defined in claim 32 wherein the taper at the distal region of the main wire is continuous.

44. A guide wire as defined in claim 32 wherein the torsionally rigid means comprises said main wire being formed from a solid rod.

45. A guide wire as defined in claim 32 wherein said torsionally rigid means comprises said guide wire being formed from a solid walled tube.

46. A guide wire as defined in claim 32 wherein said torsionally rigid means comprises said main wire being formed from a solid rod.

47. A guide wire as defined in claim 32 wherein said torsionally rigid means comprises said main wire being formed from a solid walled tube.

48. A guide wire as defined in claim 32 wherein the distal end of guide wire includes a bendable safety wire in the spring, the safety wire being adapted to be bent to said set curved configuration.

49. A guide wire as defined in claim 32 further comprising a distal spring extension at the distal end of the spring, the extension extending distally beyond the distal end of the main wire.

50. A steerable small diameter guide wire having a proximal end and a distal end comprising:
   a main wire having a proximal end and a distal region;
   a helically wound spring connected to the distal region of the main wire, the length of the spring comprising a relatively short portion of the overall length of the guide wire and the main wire comprising the major portion of the overall length of the guide wire;
   the spring being formed at least in part from a material having a high radiopacity;
   each of said main wire and spring having a maximum diameter which does not exceed 0.020 inches;
   the distal end of the guide wire being constructed to be bendable to a set curved configuration and to retain that set curve when relaxed, said bendable distal end being sufficiently flexible so as to adapt to and follow the contours of a patient's blood vessel;
   the guide wire having means sufficiently torsionally rigid along its length for transmitting to the distal end of the guide wire substantially all of the angular rotation applied to the proximal end of the guide wire thereby enabling the guide wire with prebent distal end to be controllably directed to selected branches of a patient's vascular system.

51. A guide wire as defined in claim 5 wherein the spring is formed from an alloy which includes a major proportion of platinum.

52. A guide wire as defined in claim 50 wherein said torsionally rigid means comprises said main wire being formed from a solid rod.

53. A guide wire as defined in claim 50 wherein said torsionally rigid means comprises: said main wire being formed from a solid walled tube.

54. A guide wire as defined in claim 50 wherein the outer diameter of each of the main wire and spring are substantially the same.

55. A guide wire as defined in claim 51 wherein the distal end of the guide wire includes a bendable safety wire within the spring, the safety wire being adapted to be bent to and retain said set curve.

56. A guide wire as defined in claim 50 further comprising a distal spring extension at the distal end of the spring, the extension extending beyond the distal end of the main wire.

57. A set for introducing a balloon dilatation catheter and for performing a balloon dilatation in a blood vessel comprising:
   a guide wire as defined in claim 50; and
   a balloon dilatation catheter having a main lumen which is receptive to the guide wire, said main lumen being open at the distal end of the catheter.

58. A set as defined in claim 57 wherein the main lumen in the balloon dilatation catheter is larger in cross-section than the guide wire whereby a flow passage may be maintained within the balloon catheter for infusion of liquids and pressure measurements without requiring removal of the guide wire.

59. A set as defined in claim 58 wherein the main lumen of the catheter has a different cross-sectional shape than that of the guide wire.

60. A set as defined in claim 59 wherein the guide wire is circular in cross-section and the main lumen of the catheter is D-shaped in cross-section.

61. A set as defined in claim 57 wherein the outer diameter of the dilatation catheter is not greater than of the order of 0.050 inches.

62. A set as defined in claim 58 wherein said guide wire is circular in cross-section and wherein said main lumen is non circular in cross-section.

63. A set as defined in claim 58 wherein the cross-section defined by the guide wire is not greater than about 50 percent of the cross-sectional area of the main lumen in the catheter.

64. A set of a small diameter catheter and steerable guide wire for use therewith comprising:
   a guide wire as defined in claim 50; and
   a catheter having a lumen receptive to the guide wire, the lumen being open at the distal end of the catheter, said catheter having an outer diameter not greater than of the order of 0.050 inches.

65. A steerable small diameter guide wire having a proximal end and a distal end comprising:
   a main wire having a proximal end and a distal region;
   a helically wound spring connected to the distal region of the main wire, the length of the spring comprising a relatively short portion of the overall length of the guide wire and the main wire comprising the major portion of the overall length of the guide wire;
   each of said main wire and spring having a maximum diameter which does not exceed 0.020 inches;
   the distal end of the guide wire being constructed to be bendable to a set curved configuration and to retain that set curve when relaxed, said bendable distal end being sufficiently flexible so as to adapt to and follow the contours of a patient's blood vessel;
   the guide wire having means sufficiently torsionally rigid along its length for transmitting to the distal end of the guide wire substantially all of the angular rotation applied to the proximal end of the guide wire thereby enabling the guide wire with prebent distal end to be controllably directed to selected branches of the vascular system.

66. A guide wire as defined in claim 65 wherein the torsionally rigid means comprises: said meain wire being formed from a solid rod.

67. A guide wire as defined in claim 65 wherein the torsionally rigid means comprises: said main wire being formed from a solid walled tube.

68. A guide wire as defined in claim 68 wherein the outer diameter of each of the main wire and spring are substantially the same.

69. A set for introducing a balloon dilatation catheter and for performing a balloon dilatation in a blood vessel comprising:
   a guide wire as defined in claim 65; and
   a balloon dilatation catheter having a main lumen which is receptive to the guide wire, said main lumen being open at the distal end of the catheter.

70. A set of a small diameter catheter and steerable guide wire for use therewith comprising:
   a guide wire as defined in claim 65, and
   a catheter having a lumen receptive to the guide wire, the lumen being open at the distal end of the catheter, said catheter having an outer diameter not greater than of the order of 0.050 inches.

* * * * *

UNITED STATES PATENT AND TRADEMARK OFFICE
CERTIFICATE OF CORRECTION

PATENT NO. : 4,545,390

DATED : October 8, 1985

INVENTOR(S) : James J. Leary

It is certified that error appears in the above—identified patent and that said Letters Patent is hereby corrected as shown below:

Col. 2, line 4, "possible" should read --impossible--.
Col. 4, line 51, "wire" should read --wire 10--.
Col. 12, line 23, "claim 32" should read --claim 21--; line 26, "claim 32" should read --claim 21--; line 63, "claim 5" should read --claim 50--.
Col. 13, line 7, "claim 51" should read --claim 50--.
Col. 14, line 33, "claim 68" should read --claim 65--.
Col. 14, line 28, "meain" should read --main--.

The following U.S. patent documents should be included in the list of References Cited as follows:

| | | | |
|---|---|---|---|
| 3,416,531 | Edwards | 3,757,768 | Kline |
| 3,452,742 | Muller | 3,773,034 | Burns |
| 3,470,876 | Barchilon | 3,841,308 | Tate |
| 3,503,385 | Stevens | 3,906,938 | Fleischhacker |
| 3,521,620 | Cook | 3,973,556 | Fleischhacker |
| 3,552,384 | Pierie | 4,003,369 | Heilman |
| 3,612,058 | Ackerman | 4,020,829 | Willson |
| 3,749,086 | Kline | 4,080,706 | Heilman |

Signed and Sealed this

First Day of July 1986

[SEAL]

Attest:

DONALD J. QUIGG

Attesting Officer    Commissioner of Patents and Trademarks